(12) United States Patent
Berner

(10) Patent No.: US 9,017,667 B2
(45) Date of Patent: *Apr. 28, 2015

(54) DOSAGE FORMS THAT FACILITATE RAPID ACTIVATION OF BARLEY PROTEASE ZYMOGEN

(75) Inventor: Bret Berner, Half Moon Bay, CA (US)

(73) Assignee: Alvine Pharmaceuticals, Inc., San Carlos, CA (US)

( * ) Notice: Subject to any disclaimer, the term of this patent is extended or adjusted under 35 U.S.C. 154(b) by 264 days.

This patent is subject to a terminal disclaimer.

(21) Appl. No.: 13/123,219

(22) PCT Filed: Oct. 9, 2009

(86) PCT No.: PCT/US2009/005535
§ 371 (c)(1),
(2), (4) Date: May 26, 2011

(87) PCT Pub. No.: WO2010/042203
PCT Pub. Date: Apr. 15, 2010

(65) Prior Publication Data
US 2011/0236369 A1     Sep. 29, 2011

Related U.S. Application Data

(60) Provisional application No. 61/104,607, filed on Oct. 10, 2008.

(51) Int. Cl.
| | | |
|---|---|---|
| A61K 38/48 | (2006.01) | |
| A61K 9/20 | (2006.01) | |
| A61K 9/48 | (2006.01) | |
| A61K 9/50 | (2006.01) | |
| C12N 9/50 | (2006.01) | |
| A61K 9/16 | (2006.01) | |

(52) U.S. Cl.
CPC ........... *A61K 38/4873* (2013.01); *A61K 9/1623* (2013.01); *A61K 9/2013* (2013.01); *A61K 9/2077* (2013.01); *A61K 9/2095* (2013.01); *A61K 9/4858* (2013.01); *A61K 9/5042* (2013.01); *A61K 9/5084* (2013.01); *C12N 9/50* (2013.01)

(58) Field of Classification Search
None
See application file for complete search history.

(56) References Cited

U.S. PATENT DOCUMENTS

| | | | |
|---|---|---|---|
| 4,601,896 | A | 7/1986 | Nugent |
| 5,316,772 | A | 5/1994 | Jurgens, Jr. et al. |
| 5,609,590 | A | 3/1997 | Herbig et al. |
| 5,697,922 | A | 12/1997 | Thombre |
| 6,068,853 | A | 5/2000 | Giannos et al. |
| 7,303,871 | B2 | 12/2007 | Hausch et al. |
| 7,320,788 | B2 | 1/2008 | Shan et al. |
| 7,399,772 | B2 | 7/2008 | Phillips |
| 2005/0244504 | A1 | 11/2005 | Little et al. |
| 2005/0249719 | A1 | 11/2005 | Shan et al. |
| 2007/0154547 | A1 | 7/2007 | Flanner et al. |
| 2007/0196491 | A1 | 8/2007 | Venkatesh |
| 2007/0197439 | A1* | 8/2007 | Zhu et al. ........................ 514/12 |
| 2007/0275036 | A1* | 11/2007 | Green, III et al. ............ 424/439 |
| 2008/0193436 | A1 | 8/2008 | Shan et al. |

FOREIGN PATENT DOCUMENTS

| | | |
|---|---|---|
| WO | 2005/107786 | 11/2005 |
| WO | 2007/044906 | 4/2007 |
| WO | 2008/115411 | 9/2008 |
| WO | 2008/115428 | 9/2008 |
| WO | 2009/004791 | 1/2009 |

OTHER PUBLICATIONS

Bethune M.T. et al., Heterologous Expression, Purification, Refolding, and Structural-Functional Characterization of EP-B2, a Self-Activating Barley Cysteine Endoprotease, Chemistry & Biology, 2006, vol. 13, pp. 637-647.*
McQueney M.S. et al., Autocatalytic Activation of Human Cathepsin K, The Journal of Biological Chemistry, 1997, vol. 272, No. 21, pp. 13955-13960.*
Gass J. et al., Effect of Barley Endoprotease EP-B2 on Gluten Digestion in the Intact Rat, The Journal of Pharmacology and Experimental Therapeutics, 2006, vol. 318, No. 3, pp. 1178-1186.*
Al-Janabi; et al., "Kinetics and Mechanism of Pepsinogen Activation", The Journal of Biological Chemistry (1972), 247(14):4628-4632.
Silverburg; et al., "Enzymatic activities of activated and zymogen forms of human Hageman factor (factor XII)", Blood (1982), 60:64-70.

* cited by examiner

*Primary Examiner* — Satyendra Singh
(74) *Attorney, Agent, or Firm* — Bozicevic, Field & Francis LLP; Pamela J. Sherwood

(57) ABSTRACT

The therapeutic efficacy of zymogen proteins for oral administration is improved by including in the formulation one or more excipients that optimize pH and other reaction conditions for rapid activation of the zymogen shortly after ingestion.

10 Claims, 2 Drawing Sheets

DOSAGE FORMS THAT FACILITATE RAPID ACTIVATION OF BARLEY PROTEASE ZYMOGEN

BACKGROUND OF THE INVENTION

1. Field of the Invention

This invention provides methods and compositions related to the oral administration of zymogen forms of enzymes for therapeutic purposes. The invention therefore relates to the fields of biology, molecular biology, chemistry, pharmacology, and medicine.

2. Description of Related Disclosures

The oral delivery of proteins or enzymes to the gastrointestinal (GI) tract is problematic as a result of poor protein stability due to both gastric pH and proteolytic digestion by GI enzymes as well as poor absorption. A natural solution to aid protein stability is the use of proenzymes or zymogens (these terms are used interchangeably herein to refer to an inactive precursor of an enzyme) rather than the active enzyme. Zymogens may be more stable than the corresponding enzyme itself, as when, for example, an enzyme can cleave itself into inactive fragments. The activation process of a zymogen may involve, for example, a change to the active site or exposure of an active site through cleavage of a peptide bond. There are abundant examples of zymogens in nature, including pepsinogen, trypsinogen, chymotrypsinogen, prolipase, propapain, many caspases, some lipases and certain amylases, and many members of the coagulation and complement system.

Other zymogens of interest include certain cysteine proteases. For example, cysteine endoprotease (EP) B2 from barley is a zymogen. This barley derived protease and other similar proteases derived from the germinating seeds of the gluten-containing cereals have been identified as effective agents for the detoxification of gluten, the causative agent in Celiac sprue and dermatitis herpetiformis (see U.S. Pat. No. 7,303,871, incorporated herein by reference). A modified, recombinant form of the barley-derived zymogen called "ALV001" (the active form of this enzyme is termed "ALV001*" herein) has been used as part of a combination enzyme therapy (including a prolyl endopeptidase (PEP), such as *Sphingomonas capsulata* PEP) for oral administration to Celiac sprue and dermatitis herpetiformis patients to aid in the digestion of gluten before it can exert its toxic effects in these patients (see U.S. Pat. No. 7,320,788; U.S. Patent Application Publication No. 20080193436; PCT Patent Publication No. 2008/115428; PCT Patent Publication No. 2008/115411; and PCT patent application US2009/004791, each of which is incorporated herein by reference). The ALV001 zymogen is inactive and becomes active (converts to ALV001*) below pH 5 but is not activated at a higher pH. Pepsinogen, another zymogen of a cysteine protease, depends on gastric acidity to be activated to pepsin. The reference Janabi et al. (J. Biol. Chem, 247, 4626-4632, 1972) reports that the first-order catalysis of pepsin generation below pH 3 is rapid and intramolecular while it is lower and predominantly intermolecular above pH 4. Propapain, a third example of a proenzyme of a cysteine protease, is activated by an intramolecular rearrangement of the thiol disulfide active site.

Achieving therapeutic efficacy via oral administration of a zymogen can be a balancing act between the stability of the protein, with its rapid degradation by gastric acidity and proteolysis by GI enzymes, and activation to the active enzyme form. Prior to administration, stability of the protein during storage can be aided by use of a more stable zymogen form. Gastric pH in the fasting state is typically quite acidic in the range of pH 2 (between 1.5 and 2.8) and can be raised in the postprandial state to a pH in the range of 4 to 5 or even higher, and then may return to acidic pH within 45 minutes to 1 or 2 hours, depending on the buffering capacity of the meal. With the window and variation of postprandial pH, a zymogen may not be activated to the enzyme form optimally or at all, as they are subjected concurrently to rapid degradation in the stomach. A dosage form that can provide optimal timing for the activation of the zymogen to maximize its activity and duration of activity in the stomach can dramatically improve the efficacy of the therapy intended by administration of that dosage form.

A number of dosage forms that vary release or stability with pH have been discussed in the art. U.S. Pat. No. 4,601,896 describes a capsule consisting of collagen and an activated collagenase to protect therapeutic agents and specifically digestive enzymes from degradation by gastric acidity. The enzymes are reportedly spared degradation in the stomach by delaying their release from the dosage form until it reaches the intestine. Enteric coatings and alkaline buffers were cited as other approaches to avoid gastric degradation. U.S. Pat. No. 5,316,772 and U.S. Patent Application Publication No. 20070154547 describe the use of pH dependent enteric coatings to deliver a drug to different regions of the GI tract.

A number of other dosage forms from which drug release is triggered by changes in pH have been described. U.S. Pat. No. 5,609,590 describes an osmotic bursting device in which the release of drug is triggered by a pH sensitive coating in the range of pH 3 to 9. U.S. Pat. No. 6,068,853 describes a transdermal dosage form where the driving force for drug release oscillates with pH, and the system is manually activated by mixing the contents of two reservoir compartments prior to application to the skin. U.S. Patent Application Publication No. 20050244504 describes pH triggered particles for delivering agents into an acidic environment, in particular, intracellularly in lysosomes. U.S. Pat. No. 7,399,772 describes the use of buffer with proton pump inhibitors for providing stability in the GI tract. U.S. Patent Application Publication No. 20070196491 describes the addition of an organic acid to an immediate release dosage form to improve the solubility of poorly soluble weak basic drugs with an aqueous solubility at pH 6.8 of less than 200 μg/ml. The patent reports that the addition of a free acid to a poorly soluble basic drug may be used to modify its rate of release.

There remains a need for pharmaceutical formulations and unit dosage forms that provide not only improved stability of a zymogen in the stored dosage form but also rapid activation of the zymogen in the fed stomach. The present invention meets this and other needs.

SUMMARY OF THE INVENTION

This invention provides methods, pharmaceutical formulations, and unit dosage forms that provide for the rapid activation of a proenzyme (zymogen) drug shortly after oral administration. In one embodiment, the proenzyme drug is activated within a few minutes of oral administration.

In a first aspect, the present invention provides pharmaceutical formulations of proenzyme drugs that incorporate one or more excipients that facilitate activation of the proenzyme in the stomach by ensuring that the pH in the stomach, or at least in the environment immediately surrounding the proenzyme in the disintegrating dosage form in the stomach, is maintained at a pH that facilitates activation of the proenzyme.

Suitable excipients include, without limitation, one or more of: acids and/or acidic buffer systems; antioxidants; and anionic polymers.

In a second aspect, the present invention provides unit dosage forms of the formulations of the invention. In a first embodiment, the dosage form comprises the proenzyme and one or more excipients that facilitate activation of the proenzyme in the stomach by ensuring that the pH in the stomach is maintained at a pH that facilitates activation of the proenzyme. In a second embodiment, the dosage form is configured such that the pharmaceutical formulation is in a matrix or shell or capsule that degrades in a manner that ensures that the pH of the environment immediately surrounding the proenzyme in the disintegrating dosage form in the stomach is maintained at a pH that facilitates activation of the proenzyme.

Thus, the pharmaceutical formulations and dosage forms thereof incorporate one or more excipients that set the pH, either in the dosage form, or in all or at least a part of the surrounding gastrointestinal fluid of the stomach, at a pH appropriate for rapid activation of the proenzyme, for example, a pH in the range of about 2 to about 5, or a pH in the range of about 3 to about 4. Activation of the proenzyme occurs upon disintegration of the dosage form or during ingress or uptake of water (GI fluid) by the dosage form (or particles in the dosage form) and within a few minutes prior to or concurrently with or shortly after release of the enzyme into the stomach or elsewhere in the stomach.

In one embodiment of the invention, the proenzyme is a cysteine protease capable of digesting a gluten peptide that is toxic to a Celiac sprue patient into non-toxic fragments, either alone or in combination with another protease. In one embodiment, the cysteine protease is barley endoprotease EPB2 or a modified form of that protease, and may be a recombinant version of either. In one embodiment, the proenzyme is ALV001. The activation of ALV001 to ALV001* is rapid below pH 5 and slower (or practically non-existent, depending on the pH) at a pH of 5 or above. By incorporating one, two, three or more excipients, e.g. acids and/or acidic buffer systems; antioxidants; and anionic polymers into the pharmaceutical formulation and dosage form, the rate of activation can be increased substantially from what it would have been using previously available dosage forms, particularly in the fed stomach, where the pH can be pH 5 or above.

In one embodiment of the invention, a citric or acetic acid, or their corresponding buffers, is used as an excipient to modulate the pH upon exposure of the proenzyme to water to a pH range that allows for rapid activation of the proenzyme. If a capsule embodiment of the invention is employed, the gastric fluid starts to enter the capsule and, as the acid or buffer dissolves, it establishes a pH in the desired range. For a tablet, permeation of water into the tablet, potentially including a controlled-release polymer, can set the initial pH to this range to activate the proenzyme. Alternatively sufficient acid or buffer can be released into the surrounding gastrointestinal fluid along with the proenzyme to establish the desired pH range and activate the enzyme.

In related embodiments, the pharmaceutical formulations and dosage forms comprise an antioxidant in combination with an acid or buffer. The antioxidant activity may be provided by the acid or buffer, e.g. using ascorbic acid, etc., or the antioxidant activity may be provided by a second antioxidant agent.

In another embodiment, the pharmaceutical formulations and dosage forms comprise an anionic polymer in combination with an acid or buffer, and optionally including an antioxidant. The anionic polymer allows increased activation even at suboptimal pH levels.

In a third aspect, the present invention provides a method for preventing and/or treating Celiac sprue and/or dermatitis herpetiformis in a patient, said method comprising the step of orally administering a zymogen form of a protease capable of degrading gluten into non-toxic fragments in a pharmaceutical formulation of the invention or unit dosage form of the same to said patient contemporaneously with the patient's ingestion of a gluten-containing foodstuff.

In a fourth aspect, the present invention provides a method for improving the therapeutic efficacy of a proenzyme drug orally administered to a patient, the method comprising administering the drug in combination with one or more excipients that provide, upon oral ingestion, conditions suitable for activation of the drug. The unit dosage forms of the pharmaceutical formulations of the invention are ideally suited for practice of this method. The dosage form is applicable to treatment of mammals including, but not limited to humans.

DETAILED DESCRIPTION OF THE INVENTION

Figure 1:
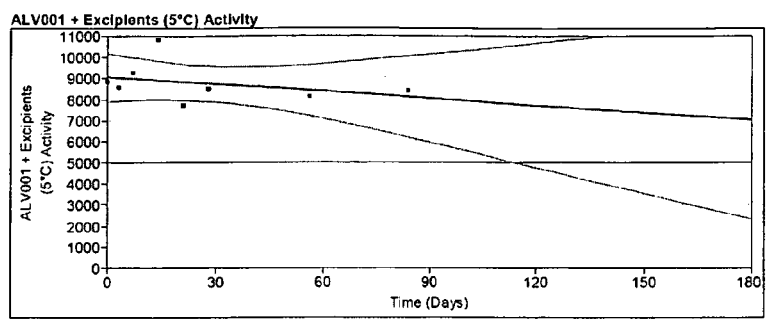
FIGS. 1A-1D. Enzyme stability at 5° C. (A, B) and 25° C. (C, D).
Figure 1:
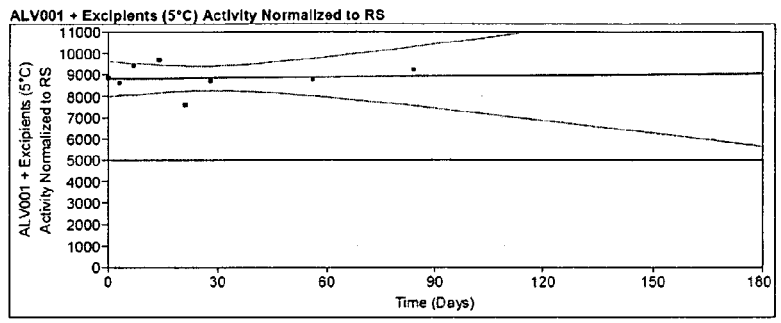
Figure 1:
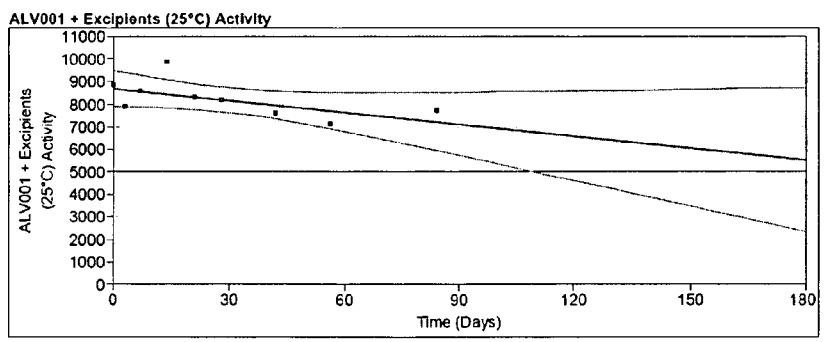
Figure 1:
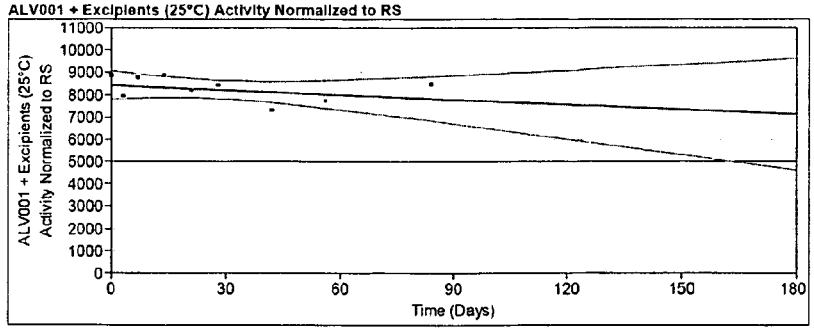

In the current art of oral delivery (the administration of a substance by mouth, i.e., oral administration) of proteins, the focus has been on protecting against the potential instability of the orally ingested protein to acid or to proteolysis by digestive/GI enzymes. Methods and systems for providing a timed mechanism of activation of an administered zymogen have not been the focus of significant effort prior to the present invention. The advantage of such activation can be particularly significant for the oral delivery of protease or other degradative enzymes to the stomach for the purpose of increasing the time available for proteolysis (or other degradative activity) and for coordinating the timing of activation and active life between two or more enzymes in a combination enzyme product. The present invention arose at least in part from the discovery that some individuals have a gastric pH of greater than 5 postprandially, which prevents optimal activation of zymogen proteases such as, for example, ALV001, that require a lower pH, for optimal activation. To be effective in the detoxification of gluten, ALV001 must be converted to the active ALV001* prior to either gastric emptying or proteolytic degradation of ALV001. After activation, exposure of ALV001* to low pH may result in rapid degradation of the activated enzyme. While high postprandial pH, if not temporarily modulated, may be detrimental to the activation of the zymogen, for ALV001* this high postprandial pH is beneficial for improved enzyme activity and stability and, therefore, for maximizing the therapeutic effect of the drug.

The present invention provides pharmaceutical formulations and unit dosage forms that comprise a zymogen drug or nutraceutical and one or more excipients that provide for an optimal pH range (such as a pH of from about 2 to about 5, or from about 3 to about 5, or from about 3 to about 4.8), within the local environment of the dosage form or particle contained in the dosage form or in at least part, if not all, of the surrounding gastrointestinal fluid in the stomach for at least a few minutes after oral administration but prior to or concurrent with release of the zymogen into the stomach. Thus, an environment permissive for proenzyme activation is provided prior to or concurrent with release from the dosage form. Excipients may also be incorporated into the dosage form, which enhance activation and/or stability of the proenzyme although not necessarily having an effect on pH, include antioxidants, and/or anionic polymers.

The present invention is illustrated with reference to a zymogen drug called ALV001, which is a recombinant, modified form of cysteine endoproteinase B1 from barley. As noted above, U.S. Pat. Nos. 7,320,788 and 7,303,871 describe the use of proteases termed glutenases, including ALV001, alone and in combination, as orally administered enzymes to digest gluten for treatment of or prevention of symptoms due to Celiac sprue and/or dermatitis herpetiformis. The timing of activation of proenzymes of these enzymes can affect their ability to digest gluten, and this is also true of combination products, composed of two or more glutenases, one or both of which may be proenzymes, as described in these patents.

The ingestion of gluten, a common dietary protein present in wheat, barley and rye, causes disease (Celiac sprue and dermatitis herpetiformis) in sensitive individuals. Gluten is a complex mixture of glutamine- and proline-rich glutenin and prolamine molecules. Ingestion of gluten by sensitive individuals (Celiac sprue and dermatitis herpetiformis patients) produces flattening of the normally luxurious, rug-like, epithelial lining of the small intestine known to be responsible for efficient and extensive terminal digestion of peptides and other nutrients. Clinical symptoms of Celiac sprue include fatigue, chronic diarrhea, malabsorption of nutrients, weight loss, abdominal distension, anemia, as well as a substantially enhanced risk for the development of osteoporosis and intestinal malignancies (lymphoma and carcinoma). The disease has an incidence of approximately 1 in 200 in European populations. Dermatitis herpetiformis, a chronic eruption characterized by clusters of intensely pruritic vesicles, papules, and urticaria-like lesions, is a related disease and can be viewed as the same disease with significant dermatologic manifestation of symptoms. IgA deposits occur in almost all normal-appearing and perilesional skin of dermatitis herpetiformis patients. Asymptomatic gluten-sensitive enteropathy is found in 75 to 90% of dermatitis herpetiformis patients and in some of their relatives. Onset of the disease is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients. Dapsone, sulfapyridine and colchicines are sometimes prescribed for relief of itching due to dermatitis herpetiformis. As noted above, Celiac sprue and dermatitis herpetiformis are generally considered to be the same or simply different manifestations of the same underlying autoimmune disease, and the antibodies found in the patients indicate an immunological basis of the disease. For example, antibodies to tissue transglutaminase (tTG) and gliadin appear in almost 100% of the patients with active Celiac sprue, and the presence of such antibodies, particularly of the IgA class, has been used in diagnosis of the disease.

The large majority of Celiac sprue and dermatitis herpetiformis patients express the HLA-DQ2 [DQ(a1*0501, b1*02)] and/or DQ8 [DQ(a1*0301, b1*0302)] molecules. It is believed that intestinal damage is caused by interactions between specific gliadin oligopeptides and HLA-DQ2 or DQ8, which in turn induce proliferation of T lymphocytes in the sub-epithelial layers of the intestine. T helper 1 cells and cytokines apparently play a major role in a local inflammatory process leading to villus atrophy of the small intestine.

At the present time, the only treatment for Celiac sprue is the strict avoidance of all foods containing gluten, although, as discussed below, clinical trials of glutenases are ongoing. While gluten withdrawal has transformed the prognosis for children diagnosed with Celiac sprue and substantially improved it for adult patients, some people still die of the disease, mainly adults who had severe disease when diagnosed. An important cause of death is lymphoreticular disease (especially intestinal lymphoma). Apparent clinical remission is often associated with histologic relapse that is detected only by review biopsies or by increased EMA titers.

Gluten is so widely used, for example in commercial soups, sauces, ice creams, hot dogs, and other foods, that patients need detailed lists of foodstuffs to avoid and expert advice from a dietitian familiar with Celiac sprue. Ingesting even small amounts of gluten may prevent remission or induce relapse. Supplementary vitamins, minerals, and hematinics may also be required, depending on the degree of deficiency experienced by a particular patient. A few patients respond poorly or not at all to gluten withdrawal, and are characterized as having a refractory form of the disease. In the latter case, oral corticosteroids (e.g., prednisone 10 to 20 mg bid) may induce response.

Perhaps the most promising new therapy in clinical development is the use of glutenases, as described in U.S. Pat. Nos. 7,320,788 and 7,303,871 (incorporated herein by reference; see also PCT Patent Application No. US2009/004791 and PCT Patent Publication Nos. 2008/115411, 2008/115428, 2007/044906, and 2007/047303, each of which is incorporated herein by reference) to prevent and/or treat the symptoms of Celiac sprue and/or dermatitis herpetiformis by decreasing the levels of toxic gluten oligopeptides in foodstuffs, either prior to or after ingestion by a patient. These patent publications and application disclose that certain gluten oligopeptides are resistant to cleavage by gastric and pancreatic enzymes, that the presence of such peptides in the small intestine results in toxic effects in Celiac sprue (and dermatitis herpetiformis) patients, and that enzymatic treatment can remove such peptides and prevent their toxic effects. By digestion with glutenases, these toxic oligopeptides are cleaved into non-toxic fragments, thereby preventing or relieving their toxic effects in Celiac sprue and dermatitis herpetiformis patients.

One candidate product in clinical development is called "ALV003" and is composed of two proteases. The efficacious treatment of Celiac sprue with this combination of enzymes, the zymogen, ALV001, and the second active enzyme, ALV002 (a recombinant, modified version of *Sphingomonas capsulata* PEP), depends critically on maintaining the enzymes in the stomach in active form until the gluten is degraded into non-toxic fragments. ALV001, the unactivated zymogen of ALV001*, is inactive and becomes active (converts to ALV001*) below pH 5, but will not be activated at higher pH. The mechanism of activation of ALV001, like other cysteine proteases, is primarily intramolecular. It is rapidly activated at a pH of from about pH 3 to almost pH 5. It is unstable at lower pH (below pH 3).

In a combination dosage form, the use of ALV001 provides an advantage in stability over the use of ALV001*, in that the proenzyme is more stable and, unlike ALV001*, does not digest and degrade ALV002. In order to digest gluten before the stomach empties and before the zymogen ALV001 is degraded, the zymogen must be rapidly activated upon administration, i.e. at a pH of from about 3 to about 5. However, in the fed state the pH of the stomach may exceed pH 5 in a number of individuals.

The present invention provides in some embodiments a dosage form that provides for reliable proenzyme activation in the stomach, including, for example, a dosage form for reliable pH dependent proenzyme activation. In one embodiment, the dosage form is a capsule, preferably a hypromellose capsule, containing a zymogen, such as ALV001, and an acid or buffer. As used herein, "buffer" refers to a mixture of either a weak acid and its conjugate base or a weak base and its conjugate acid that, when in solution, resists changes in pH. Acids of interest include, without limitation, maleic acid, fumaric acid, tartaric acid, citric acid, oxalic acid, succinic acid, gallic acid, lactic acid, malic acid, and ascorbic acid, any of which may be present at a dose of from about 25 to about 250 mg. Buffers of interest include, without limitation, maleic acid and maleate, fumaric acid and fumarate, tartaric acid and tartarate, citric acid and citrate, oxalic acid and oxalate, succinic acid and succinate, gallic acid and gallate; ascorbic acid and ascorbate, and malic acid and lactate. Such buffers may be provided at a dose of from about 25 to about 250 mg, for example at about 25, about 50, about 100, about 150, about 200, about 250 mg, where the ratio of components is selected to provide desired pH and buffering capacity.

Standard tables of buffers may be used to determine quantities of components for a buffer useful in the pharmaceutical formulations and dosage forms of the invention. For example, 35 mg of sodium citrate and 100 mg of citric acid will give a pH of 3.3, and 70 mg of sodium citrate and 200 mg of citric acid will also give a pH of 3.3 with twice the buffer capacity; 42.6 mg of sodium citrate and 179.6 mg of citric acid will give a pH of 3; 110 mg of sodium citrate and 131 mg of citric acid will give a pH of 4; and 56.4 mg of sodium acetate and 35.2 mg of acetic acid will give a pH of 4.6.

The acid or buffer is present at a quantity sufficient to overwhelm briefly any other buffer capacity in the dosage form, including other additional buffers for protein stability, such as Tris buffer. Following administration of the capsule, once water begins its ingress or uptake, and before or during the dissolution of the capsule, the said acid or buffer is sufficient to set the pH within the capsule at a level between about pH 2 to about pH 5, for example between 3 and 4.8. Because the stability of ALV001 may also depend on the pH not remaining below pH 3 for too long a time, the concentration of acid or buffer, the rate of release of the enzyme, or the addition of a second buffer, such as Tris buffer, may be used in accordance with the invention to provide the right balance for activation of the zymogen prior to significant degradation of the enzyme.

In some embodiments of the invention, at least about 20% of the acid or buffer is released within about 15 minutes following ingestion, i.e. immersing the dosage form in gastric fluid. In some embodiments, at least about 30% of the acid or buffer is released within about 20 minutes following ingestion, i.e. immersing the dosage form in gastric fluid, where the release is optionally in a pulsatile or gradual release profile.

Hypromellose capsules, which can obtained, for example, from Qualicaps, size 0, were observed to open (disintegrate) in saline at pH 1.2 between 3:38 and 4:49 minutes; and at pH 5.4 in acetate buffer between 4:08 and 5:42 minutes.

The formulations and dosage forms of the invention may comprise an antioxidant; usually, when present, the antioxidant is provided in addition to the acid or buffer. Pharmaceutically acceptable antioxidants are well known to the person skilled in the art and are described in the technical literature forming the general common knowledge. A source of information, for example, can be found in "Remington's Pharmaceutical Sciences Handbook", Mack Pub. N.Y. U.S.A. Antioxidants of interest include, without limitation, ascorbic acid, its salts and esters, Vitamin E, tocopherol and its salts, sodium metabisulfite, potassium metabisulfite, butylated hydroxyanisole (BHA), butylated hydroxytoluene (BHT), and the like. The use of sodium metabisulfite can be of particular benefit for many applications of the invention.

An antioxidant may be provided at an effective dose of from about 1 to about 100 mg, for example at about 2, about 5, about 8, about 10, about 15, about 20, about 25 mg, where the ratio of components is selected to provide enzyme stability. In some embodiments of the invention, the formulation or dosage form comprises an effective dose of an acid or buffer, and an effective dose of an antioxidant. For certain highly potent antioxidants, such as BHT or BHA, one can incorporate one or more of these antioxidants at the 0.01% to 0.1% level in accordance with the invention.

The formulation or dosage form of the invention may comprise a polymer, particularly an anionic polymer. Usually, when present, the polymer is provided in addition to the acid or buffer. Pharmaceutically acceptable polymers are well known to the person skilled in the art and are described in the technical literature. An effective dose of polymer increases the rate of proenzyme activation, particularly where the pH is higher than optimal, e.g. at a pH of greater than 4.5, a pH greater than 5.0, etc. The effective dose may provide for a stomach concentration of from about 3 to about 100 µg/ml polymer.

Suitable polymers include, without limitation, dextran sulfate, chondroitin, chondroitin sulfate, heparin, heparin sulfate, cellulose sulfate, xanthan, hyaluronic acid, polyacrylic acid, polyacrylamide, carboxymethylcellulose, polypropanesulfonic acid, polyglutamates, anionic chitosan derivatives, such as the succinyl derivatives, and anionic maleic anhydride copolymers and derivatives, and the like. The effective dose will vary with the potency of the polymer. For example, dextran sulfate and similar polymers may be included in a unit dose at from about 2 µg to about 5 mg, usually at a unit dose at from about 5 µg to about 100 µg. Chondroitin, heparin sulfate, and similar polymers may be included in a unit dose at from about 5 µg to about 200 µg, usually at a unit dose at from about 10 µg to about 75 µg. Polyacrylic acid, cellulose sulfate, carboxymethylcellulose, and similar polymers may be included in a unit dose at from about 50 µg to about 10,000 µg. As a result of its unusual potency and well characterized toxicity, dextran sulfate can be a preferred anionic polymer for certain applications of the invention.

Polymers may be incorporated into a formulation packaged in a capsule, to allow the proenzyme to activate inside of the capsule upon entry of fluid. A polymer may also be included when the formulation is provided in a tablet form, potentially including a controlled-release polymer, to allow pro-ALV001 (or other zymogen) to activate more efficiently within the tablet or within the stomach. The formulation may provide a few minutes, such as 1 to 15 minutes, 2 to 12 minutes, or 4 to 8 minutes, for this to occur.

One or more dosage forms may be used to deliver each dose with a meal of the enzyme. A tablet may weigh from 100 to 900 mg when compressed with B tooling or may weigh up to almost 1.5 g when compressed with D or other non-standard tooling. At this large size it becomes undesirable to swallow and sizes under 800 mg are generally preferred for ease of swallowing. Capsules may also be used, and capsules made of hypromellose with their lower water content for better protein stability are preferred. For size 0 capsules, 400 mg is an approximate maximum filling in the capsule without additional compression. A sachet may also be used where the contents of the sachet may be mixed with a drink or food and swallowed. The sachet may be designed to contain larger quantities of enzyme and excipients. The protein content in the dosage form may vary, including from, for example 10 to 80% or from 20 to 50%, of the dosage form by weight.

In one embodiment of this invention, the dosage form contains not only the zymogen and the buffer or acidic activating agent, but also a second enzyme. This second enzyme, such as, for example, ALV002, may be directly blended in with the other ingredients or separately filled into the capsules or tablets. ALV002 may be in a separate layer or section of a capsule, tablet, or sachet to improve stability from protein degradation from digestion by the activated enzyme formed from the zymogen. To aid stability, ALV002 may also be coated with an erodible coating that dissolves or degrades in gastric or intestinal fluid. Examples of an erodible coating include hypromellose, water soluble polyvinyl alcohol, polyethylene oxide, poloxamer, or fats and waxes such as beeswax, cetyl alcohol and other materials used in standard erodible, permeable sustained release coatings. This protective erodible coating may dissolve quickly or within 5 to 15 minutes after the zymogen is activated to allow the activated enzyme to digest gluten before the ALV002 provides additional digestion of gluten while decreasing the exposure of ALV002 to the harsh degradative environment of the stomach.

The pharmaceutical formulations of the invention can be in the form of, for example and without limitation, capsules, particles, particles in capsules or sachets, or tablets. The formulation can, for example and without limitation, be added to a food or drink and then administered, for example, as a sprinkled powder, sprinkles, or as a granule formulation, or as a spread in the form of a jam or paste. A capsule of low water content may be used for improved stability, and hypromellose capsules, HPMC, of any desirable size, e.g. 1, 0, or 00, can be used. Capsules can be packaged in a dry environment either with dessicant or dessicant packs or if in blisters under dry nitrogen or other dry environment.

Examples of acid activating excipients useful in the pharmaceutical formulations of the invention include, but are not limited to, one or more of malic, maleic, fumaric, tartaric, citric, oxalic, succinic, gallic, ascorbic, benzoic, boric, salicylic, glutaric, dimethylglutaric, and sorbic acids. Polymeric acids such as polyacrylic acid, polymethacrylic acid, shellac, dextrans and others may be used as the activating acidic excipient. Examples of buffer excipients include, but are not limited to, one or more of glycine, citrate, acetate, Tris, phosphate, borate, piperazine, dimethylglutarate, citrate-phosphate, and potassium biphthalate buffers. The acid and/or buffer excipients may be incorporated in separate particles, granules, or pellets that are tabletted or placed into capsules to form a dosage form that disperses into separate particles rapidly after administration. Alternatively, the acid or buffer may be blended with other excipients or excipients and the zymogen.

The pharmaceutical formulations of the invention can comprise one or more lubricants, including, but not limited to magnesium stearate, stearic acid, sodium stearyl fumarate, and sodium stearyl lactylate, glyceryl behenate, hydrogenated vegetable oil (such as hydrogenated and refined triglycerides of stearic and palmitic acids), and mixtures of these lubricants. These may be at, for example and without limitation, 0.3 to 5% of weight of the dosage form. Higher concentrations of lubricant may be used, for example, if an excipient such as mannitol is contained at a high concentration in the lyophilized powder.

The cysteine protease (or other protein active pharmaceutical ingredient) powder may be blended with lubricant or other excipients, such as a filler or binder, and granulated. If the cysteine protease (or other API) is unstable with water and temperature, then the API and any lubricant or other excipients can be roller compacted into granules, if necessary using chilled rollers for stability. One may optionally include at this step the agent that modifies or controls pH, at least for the first few minutes after the dosage form is in the GI tract, to facilitate activation of the zymogen (for example, ALV001).

Fillers and binders such as dicalcium phosphate, microcrystalline cellulose, mannitol, lactose, sucrose, and trehalose, and mixtures of such fillers, can be included and blended with the powders or included in the lyophilized or spray-dried powder preparation of the zymogen. More hydrophilic fillers, such as microcrystalline cellulose, may be avoided for certain enzymes, such as ALV001.

Controlled-release excipients may be blended into the pharmaceutical formulation or used in the manufacture of the dosage form itself to form polymeric drug-containing matrices. These matrices may be, for example, from about 0.5 or 1 mm in diameter to the size of a full tablet 10 to 12 mm in width and up to 1.8 cm or more in length. These matrices can provide extended-release into the stomach, being retained with food for ½ to 8 hours, depending on the size. These matrices may optionally be swellable in accordance with the invention. If swellable dosage forms are desired, then they are prepared in accordance with the invention by using extended-release hydrophilic polymers that include, for example and without limitation, cellulose polymers and their derivatives (such as for example, hydroxyethylcellulose, hydroxypropylcellulose, carboxymethylcellulose, and microcrystalline cellulose, polysaccharides and their derivatives, polyalkylene oxides, polyethylene glycols, chitosan, poly(vinyl alcohol), xanthan gum, maleic anhydride copolymers, poly(vinyl pyrrolidone), starch and starch-based polymers, poly(2-ethyl-2-oxazoline), poly(ethyleneimine), polyurethane hydrogels, and crosslinked polyacrylic acids and their derivatives. Further examples are copolymers of these polymers, including block copolymers and grafted polymers. Extended-release coatings can also be prepared to provide other unit dosage forms of the invention using the above polymers. When extended-release dosage forms are prepared for a zymogen, erodible polymers containing both the zymogen and the activating agent, such as citric acid or citrate or acetate buffers, can be employed so that the zymogen remains unactivated when dry and then, as the polymer imbibes water, is activated by the change in pH and eventually released into the gastric fluid by the dissolution of the polymer.

In various embodiments, the composition of a dosage form of the invention can be described by selecting one or more of the illustrative elements listed in each category in the following table. This table is merely illustrative and does not include all possible elements; furthermore, other components not represented by a category in the table can be included in a dosage form of the invention. As described above, the dosage form may further comprise a second enzyme, e.g. ALVN002, etc.

| Component | Zymogen | Weak Acid or Buffer | Lubricant | Filler | Erodible Coating | Type of dosage form |
|---|---|---|---|---|---|---|
| Examples | ALV001 Prolipase Proamylase | Citric acid Tartaric acid Fumaric acid Maleic acid Acetate buffer Citrate buffer Polyacrylic acid Polymethacrylic acid | None Sodium stearyl fumarate Magnesium stearate Stearic acid | None Mannitol Sucrose Lactose Dicalcium phosphate | None Low molecular weight hypromellose Water soluble polyvinyl alcohol PEO | Capsule Tablet Sachet Sprinkle |

The following examples describe illustrative embodiments of the invention.

EXAMPLE 1

In size 0 hypromellose capsules (Qualicaps), about 300 mg mannitol was weighed. As a buffer activation agent, 100 mg of citric acid and 35 mg sodium citrate were weighed to give a local pH of 3.3. A small quantity of dye, quinaldine red, which turns red from colorless at pH 3.2, and a small quantity of Tween 80 to dissolve the insoluble dye, were added. Six capsules were tested in a USP Type 1 paddle dissolution apparatus with sinker to avoid floating capsules at 37° C. stirred at 50 rpm in 900 ml solution. The solutions were adjusted to pH 1.2 to simulate gastric fluid without pepsin and with acetate buffer to pH 5. At pH 1.2, the dye appeared red at 5:03 to 5:59 minutes and totally dissolved 13:09 to 14:28 minutes. At pH 5, the dye changed to red at 4:51 to 5:42 minutes, and dissolution was complete at 13:21 to 14:24 minutes. This experiment demonstrates that the buffer did briefly set the local pH environment, but was quickly overwhelmed by the buffer capacity of the large volume of solution, particularly at pH 5.

EXAMPLE 2

In size 0 hypromellose capsules (Qualicaps), about 100 mg mannitol, 50 mg ALV001, 50 mg ALV002, 10 mg Tris Buffer, pH 8.5, 7 mg sucrose, 3 mg EDTA, 1 mg monothioglycerol, with these latter excipients added to improve the stability of the proteins, are filled. In addition, 250 mg citric acid are added as an activating agent to half the capsules. The activation of the ALV001 by Western blots and stability prior to dissolution are compared after dissolution in pH 5 buffer to demonstrate that the capsules containing the citric acid showed greater activation of ALV001.

EXAMPLE 3

ALV001 with its stabilizing excipients are blended with low molecular weight hypromellose as a binder, sodium stearyl fumarate as a lubricant, and citric acid as an activating agent. This blend is roller compacted to give a granulation. This granulation is then coated with about 2% by weight coating of low molecular weight hypromellose to provide a coating that dissolves in approximately 10 to 15 minutes. In size 0 hypromellose capsules (Qualicaps), these coated granules containing 25 mg ALV001, an equal quantity of uncoated ALV001 and its stabilizing excipients, and 50 mg citric acid are filled. When dissolved in modified simulated gastric fluid or pH 5 buffer, 25 mg of ALV001 are released and activated within the first ten minutes and the remainder is released and activated in 10-20 minutes.

EXAMPLE 4

About 50 mg ALV001 with dicalcium phosphate as a filler and sodium stearyl fumarate are roller compacted. About 50 mg ALV002 with dicalcium phosphate as a filler and sodium stearyl fumarate are roller compacted. Both granulations, with low molecular weight hypromellose as a binder, mannitol as filler, 150 mg of citric acid as an activating agent, and sodium stearyl fumarate are blended. The blend is placed in a Manesty Betapress with B tooling and 400 mg tablets are prepared. When immersed in pH 5 buffer for dissolution testing, the tablet rapidly dissolves, and some activation of ALV001 is observed.

EXAMPLE 5

ALV002 is combined with dicalcium phosphate and sodium stearyl fumarate and roller compacted. These granules are then coated with about 2% by weight of hypromellose to provide a coating that dissolves 10 minutes after the ALV001 is released. In size 0 hypromellose capsules (Qualicaps), about 100 mg mannitol, 50 mg ALV001, 50 mg ALV002 in the coated granules, 10 mg Tris Buffer, pH 8.5, 7 mg sucrose, 3 mg EDTA, 1 mg monothioglycerol, with these latter excipients added to improve the stability of the proteins, are filled. This dosage form when exposed to gastric fluid wets the citric acid to activate the ALV001 and about 10 minutes later releases the ALV002.

EXAMPLE 6

A spray dried ALV001 drug substance is used that contains: 242 mg Tris, 27.5 mg monothioglycerol, 146 mg EDTA, 1500 mg ALV001 protein, 250 mg mannitol, and 250 mg sucrose. Sheets were formulated by roller compaction after blending in this ratio: 420 mg of ALV001 drug substance, 233 mg sucrose, 13.3 mg sodium stearyl fumarate as lubricant, 8 mg sodium metabisulfite, 46 mg citric acid, and 20 µg dextran sulfate. Geometric mixing was used for the materials present in small amounts. Dextran sulfate could also have been spray dried onto a filler. A granulation is prepared by direct feeding of the sheets from the roller compactor. Tablets weighing approximately 500 mg are prepared on a Carver press with B tooling.

Activation of ALV001 is studied by dissolution of the granules into pH 5 buffer in a USP Type 2 (paddle) dissolution apparatus. In approximately 5 minutes the tablet is expected to disintegrate and then to dissolve. Samples are to be taken at 5 minutes and brought up to pH 7.7 with Tris buffer. These samples are expected to show active enzyme by the chromogenic assay with an activity expected to be in the range of 4000 to 5000 U/mg.

EXAMPLE 7

Granules of ALV001 from Example 6 were filled into size 0 HPMC capsules including 400 mg granules into each capsule.

EXAMPLE 8

Granules of ALV001 were blended with 25% sucrose, 2% sodium stearyl fumarate, and 6% sodium starch glycolate. Using B tooling this blend was compressed into 325 mg tablets that rapidly dissolved into individual granules.

EXAMPLE 9

The example shows the use of citric acid monohydrate for activation and sodium metabisulfite as an antioxidant. The ALV001 drug substance was lyophilized and contained approximately: 21% ALV001 protein, 39% mannitol, 20% Tris buffer, pH 8.5, 14% sucrose, 2% sodium chloride, 3% EDTA, and 1% monothioglycerol. 150 mg of enzyme (ALV001) drug substance was formulated with 300 mg. citric acid monohydrate, and 8 mg. sodium metabisulfite, placed in polypropylene bottle, and sealed in foil pouches. A chromogenic assay was measured at specified time points to assess stability, as shown in FIG. 1

EXAMPLE 10

Figure 2:
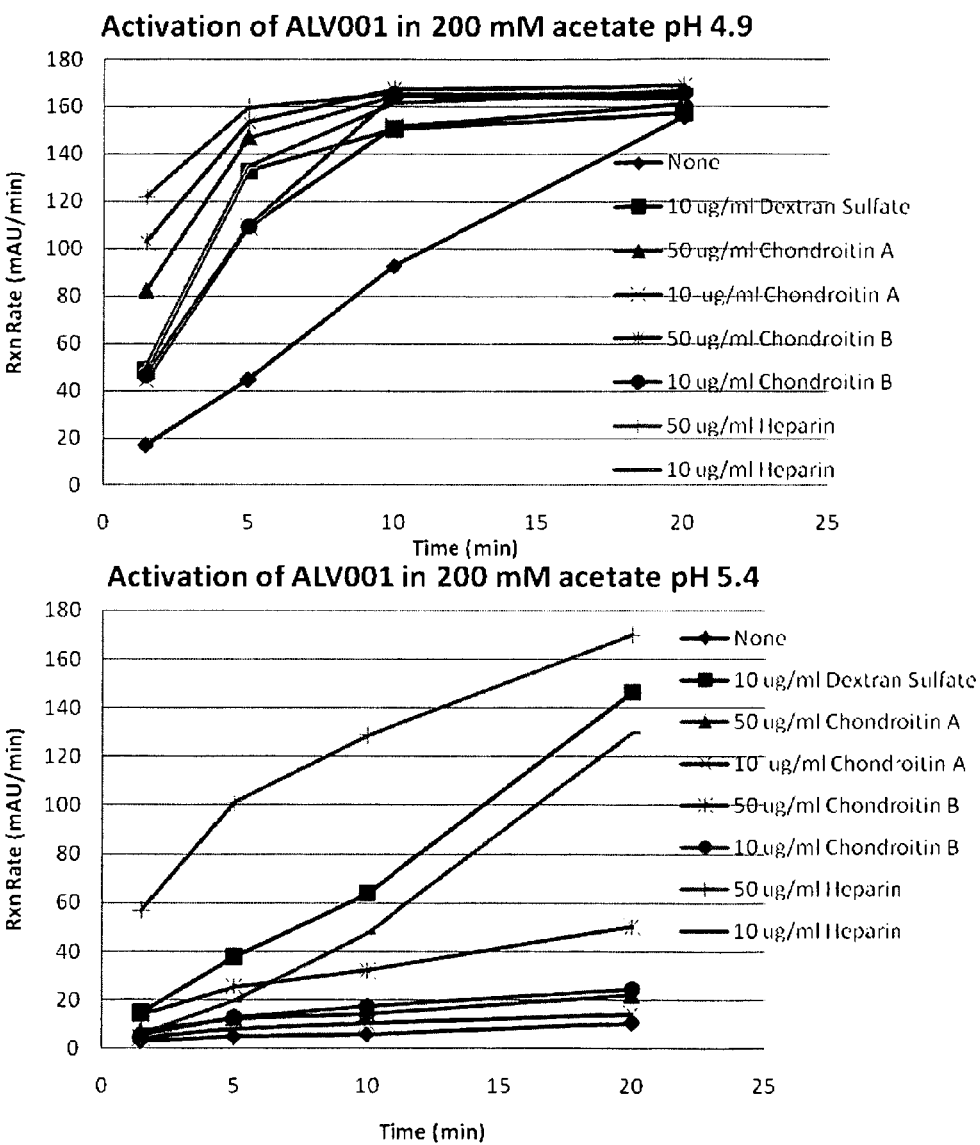
FIG. 2. 0.15 mg/ml ALV001 was incubated in 3 mg/ml pepsin in buffers with different pHs. The chromogenic activity was measured in Tris buffer pH 7.7 at the indicated time-points to determine amount of functional enzyme remaining.

ALV001 was diluted into 200 mM buffers pre-heated to 37° C. in 200 mM acetate buffer at pH 5.4. After 1.5, 5, 10, and 20 minutes, ALV001 activity was measured using the chromogenic activity assay to determine the kinetics of ALV001 activation, shown in FIG. 2.

The proteolytic activity of ALV001 at 25° C. against the chromogenic substrate Z-Phe-Arg-pNA is assessed by measuring the rate of change in the absorbance of light at 410 nm. The method is based on the release of para-nitroaniline (pNA, 4-nitroaniline) into solution, which absorbs light at 410 nm. The specification is ≥5000 u/mg for ALV001.

The proteolytic activity of ALV002 at 25° C. against the chromogenic substrate Z-Gly-Pro-pNA is assessed by measuring the rate of change in the absorbance of light at 410 nm. The method is based on the release of para-nitroaniline (pNA, 4-nitroaniline) into solution, which absorbs light at 410 nm. The specification is ≥3000 u/mg for ALV002.

The invention claimed is:

1. A unit dose of a dry pharmaceutical formulation for oral administration of an isolated barley EP-B2 protease zymogen, the formulation comprising:
    an effective unit dose of said barley EP-B2 protease zymogen comprising protein content in the range of 10 to 80% of the formulation by weight; and
    from 25 to 250 mg of an acid or acidic buffer system, which comprises one or more of
    citric acid, maleic acid, malic acid, and fumaric acid and which provides a pH suitable for activation of EP-B2 protease zymogen when the formulation is exposed to gastric fluid;
    formulated as capsules, particles or granules in capsules or sachets, or tablets.

2. The formulation of claim 1, further comprising an antioxidant.

3. The formulation of claim 1, further comprising a polymer.

4. The formulation of claim 3, wherein the polymer is an anionic polymer.

5. The formulation of claim 4, wherein the polymer is selected from the group consisting of dextran sulfate, chondroitin, chondroitin sulfate, heparin, heparin sulfate, cellulose sulfate, xanthan, hyaluronic acid, polyacrylic acid, polyacrylamide, carboxymethylcellulose, polypropanesulfonic acid, polyglutamates, anionic chitosan derivatives, and anionic maleic anhydride copolymers and derivatives.

6. The formulation of claim 5, wherein the polymer is dextran sulfate at a dose of about 2 μg to about 100 μg.

7. The formulation of claim 1, wherein the capsule is made of hypromellose.

8. The pharmaceutical formulation of claim 1, wherein at least 20% of the acid or acidic buffer system is released within 15 minutes of immersing the pharmaceutical formulation in gastric fluid.

9. The pharmaceutical formulation of claim 1, wherein at least 30% of the barley EP-B2 protease is released in a pulsatile or gradual release profile beginning at least 15 minutes after immersing the pharmaceutical formulation in gastric fluid.

10. A unit dose of a dry pharmaceutical formulation for oral administration of an isolated barley EP-B2 protease zymogen, the formulation comprising:
    an effective unit dose of said barley EP-B2 protease zymogen comprising protein content in the range of 10 to 80% of the formulation by weight; and
    from 25 to 250 mg of an acid or acidic buffer system, which comprises one or more of citric acid, maleic acid, malic acid, and fumaric acid, and from 1 to 100 mg of sodium metabisulfite;
    formulated as capsules, particles or granules in capsules or sachets, or tablets.

* * * * *